United States Patent [19]
Schoebrechts

[11] Patent Number: 6,153,803
[45] Date of Patent: Nov. 28, 2000

[54] PROCESS FOR THE PREPARATION OF HALOHYDROCARBONS

[75] Inventor: Jean-Paul Schoebrechts, Grez-Doiceau, Belgium

[73] Assignee: Solvay Societe Anonyme, Brussels, Belgium

[21] Appl. No.: 09/087,852

[22] Filed: Jun. 1, 1998

[30] Foreign Application Priority Data

Jun. 2, 1997 [BE] Belgium ............................ 09700476

[51] Int. Cl.[7] ........................... C07C 21/18; C07C 17/30
[52] U.S. Cl. ............................................. 570/172; 570/257
[58] Field of Search ..................................... 570/172, 257

[56] References Cited

FOREIGN PATENT DOCUMENTS

| | | |
|---|---|---|
| 0142041 | 5/1985 | European Pat. Off. . |
| 0729932 | 9/1996 | European Pat. Off. . |
| 1216946 | 8/1989 | Japan ..................................... 570/172 |
| WO 97/15540 | 5/1997 | WIPO . |

OTHER PUBLICATIONS

M. Asscher et al., "Chlorine Activation by Redox Transfer. Part II.[1] The Addition of Carbon Tetrachloride to Olefins", J. Amer. Chem. Soc., 1963, pp. 1887–1896.

Johannus A.M. vanBEEK et al., "Influence of the Amino Substituents of Potentially Bis Ortho Chelating Aryl Ligands $(2,6-\{R^1R^2NCH_2\}_2C_6H_3)$—on the Synthesis and Properties of Their Organonickel (II) Complexes", Inorg. Chem., 1991, pp. 3059–3068.

*Primary Examiner*—Alan Siegel
*Attorney, Agent, or Firm*—Venable

[57] ABSTRACT

Halohydrocarbons comprising at least 3 carbon atoms are obtained by reaction between a haloalkane and a haloolefin in the presence of an organonickel compound as catalyst, and optionally in the presence of a solvent. 1,1,1,3,3-Pentachlorobutane can thus be obtained in good yield under mild conditions.

11 Claims, No Drawings

PROCESS FOR THE PREPARATION OF HALOHYDROCARBONS

FIELD OF THE INVENTION

The present invention relates to a process for the preparation of halohydrocarbons comprising at least 3 carbon atoms, by catalytic reaction between a haloalkane and a haloolefin.

TECHNOLOGY REVIEW

The addition of a haloalkane to a haloolefin is a well-known reaction. However, it is sometimes difficult to control the reaction such that a single haloolefin molecule adds to a haloalkane molecule (formation of a 1:1 adduct or addition product).

Very often, copper derivatives are used to catalyse this addition reaction. For example, M. Asscher and D. Vofsi (J. Chem. Soc. 1887–1896, 1963) describe the addition of carbon tetrachloride to olefins in the presence of catalysts containing copper or ion. However, this process has the drawback of requiring long periods of heating in order to obtain the addition product in an acceptable yield.

SUMMARY OF THE INVENTION

The invention is thus directed towards a process which makes it possible to gain access, in excellent yield, to halohydrocarbons comprising at least 3 carbon atoms, in a single step and starting with readily available reagents.

Consequently, the present invention relates to the preparation of halohydrocarbons comprising at least 3 carbon atoms, by reaction between a haloalkane and a haloolefin in the presence of an organonickel compound as catalyst.

DETAILED DESCRIPTION OF THE EMBODIMENT

The organonickel compound used as catalyst in the process according to the present invention is chosen from nickel(II) salts formed with carboxylic acids such as formic acid, acetic acid, acetylacetic acid and benzoic acid, and from organometallic compounds in which the nickel is attached to an aliphatic or aromatic carbon atom, such as alkylnickels or arylnickels and nickel tetracarbonyl. The organonickel compound can also be chosen from complexes formed with neutral ligands, such as phosphines. The organonickel compound used as catalyst according to the present invention can be bound to a polymeric support, such as polysiloxanes, or can form part of a dendrimer structure formed from silanes.

Advantageously, the organonickel compound is an organometallic compound in which the nickel atom is attached to an aromatic carbon atom. Preferably, the organonickel compound is a compound of general formula $[Ni^{III}\{4-RC_6H_2(CH_2NMe_2)_2-2,6\}X]$ (referred to as formula (I) hereinbelow) in which R represents a hydrogen atom or an electron-donating group such as an amine, alkylamine, or dialkylamine function, an alcohol function or an alkoxy group, and X represents a halide ion. The organonickel compounds of general formula (I) can be obtained as described in Inorg. Chem. 1991, 30, 3059–3068.

Preferably, in the general formula (I) above, R represents a hydrogen atom or an amine group ($NH_2$) and X represents a bromide ion.

The halohydrocarbons obtained according to the process of the present invention belong in general to the chloropropane, chlorobutane or chloropentane family. The carbon atoms of the said chloropropanes, chlorobutanes and chloropentanes can also be substituted with other functional groups such as other halogen atoms (for instance bromine or iodine atoms), alkyl or haloalkyl groups, nitrile (CN) groups or carboxylic acid (COOH) groups. Chloropropanes and chlorobutanes are preferred.

Preferably, the halohydrocarbons obtained according to the process of the present invention correspond to the general formula $C_nH_{(2n+2)-p}Cl_p$ in which n is an integer and has the values 3 or 4, and p is an integer which has the values 3 to 7. Examples of compounds obtained according to the process of the present invention are 1,1,1,3,3-pentachloropropane, 1,1,1,3,3-pentachlorobutane, 1,1,1,3-tetrachloropropane, 1,1,3,3-tetrachlorobutane, 1,1,1,3,3,3-hexachloropropane and 1,1-dichloro-2-trichloromethylpropane. Among these compounds, 1,1,1,3,3-pentachloropropane, 1,1,1,3,3-pentachlorobutane and 1,1-dichloro-2-trichloromethylpropane are preferred. 1,1,1,3,3-pentachlorobutane and 1,1,1,3,3-pentachloropropane are most particularly preferred.

The haloalkanes used in the process according to the present invention are generally saturated organic compounds. They preferably have from one to three carbon atoms and preferably at least 2 chlorine atoms. They can also comprise other substituents such as other halogen atoms, alkyl groups or haloalkyl groups. As examples of haloalkanes according to the present invention, mention may be made of dichloromethane, chloroform, carbon tetrachloride, 1,1,1-trichloroethane and 1,1,2-trichloro-1,2,2-trifluoroethane. Carbon tetrachloride is most particularly preferred.

The haloolefins used in the process according to the present invention are generally derivatives of a haloethene or of a halopropene, which can themselves be optionally substituted. They can be substituted with halogen atoms, alkyl groups or haloalkyl groups, nitrile (CN) groups or carboxylic acid (COOH) groups. As nonlimiting examples of haloolefins, mention may be made of vinyl chloride, vinylidene chloride, trichloroethylene and various chloropropene isomers such as 1-chloro-1-propene, 2-chloro-1-propene and 3-chloro-1-propene. 2-chloro-1-propene is particularly suitable.

The process according to the invention can be carried out in a continuous or batchwise manner. In a batchwise process, the molar ratio between the organonickel compound used as catalyst and the haloolefin is usually greater than or equal to 0.0001. Advantageously, it is greater than or equal to 0.001. Preferably, it is greater than or equal to 0.005. The molar ratio between the organonickel compound used and the haloolefin is usually less than or equal to 1. Advantageously it is less than or equal to 0.5. Preferably it is less than or equal to 0.1.

In a continuous process, the molar ratio between the catalyst used and the haloolefin ranges approximately between the same limits as in a discontinuous process.

The molar ratio between the haloalkane and the haloolefin used can vary within a wide range. This ratio is generally greater than or equal to 0.1. Advantageously, this ratio is greater than or equal to 0.5. Preferably, it is greater than or equal to 1. Generally, this ratio is, however, less than or equal to 20. Advantageously, this ratio is less than or equal to 15. Preferably, this ratio is less than or equal to 10.

Generally, the reaction takes place at a temperature greater than or equal to room temperature. Preferably, the temperature is greater than or equal to 30° C. In general, the reaction temperature does not exceed 100° C. Preferably, the temperature is less than or equal to 70° C.

The reaction time in a batchwise process or the residence time in a continuous process depends on various parameters such as the reaction temperature, the concentration of reagents and of catalyst in the reaction mixture and their molar ratios. In general, as a function of these parameters, the residence time or the reaction time can range from 5 minutes to 10 hours.

The pressure is usually greater than or equal to atmospheric pressure and less than or equal to 15 bar.

The addition reaction is generally carried out in the liquid phase. It can be carried out in the presence of a solvent. Advantageously, the reaction solvent is a polar solvent such as an alcohol or a nitrile. Among the alcohols which can be used as reaction solvent are, in particular, methanol, ethanol, isopropanol and tertbutanol. Among the nitriles which can be used as reaction solvent are aliphatic or aromatic nitriles. Among the aliphatic nitriles are, in particular, acetonitrile, propionitrile or adiponitrile. Among the aromatic nitriles are, in particular, benzonitrile or tolunitrile. Propionitrile and adiponitrile are preferred. The amount of solvent used in the reaction is not critical. However, too dilute a solution does not favour a high yield or a high degree of conversion. Preferably, the molar ratio of the solvent to the haloolefin is greater than or equal to 0.05. Advantageously, this ratio is greater than or equal to 0.1. The molar ratio of the solvent to the haloolefin is generally less than or equal to 30. Advantageously, it is less than or equal to 20. Preferably, this ratio is greater than or equal to 1 and less than or equal to 15.

The process of the invention thus makes it possible to synthesize halohydrocarbons in a single step, starting with readily accessible reagents, with a degree of conversion of the reagents of from 75 to 100%, with a yield of from 65 to 100% and a selectivity of from 80 to 100%.

The halohydrocarbons obtained according to the process of the invention are precursors of the corresponding fluoro analogues, which can be readily obtained by treatment with hydrogen fluoride in the presence of a catalyst such as an antimony salt, a titanium salt, a tantalum salt or a tin salt.

Examples below illustrate the invention in a nonlimiting manner. In these examples, the reagents, the solvent and the catalyst were introduced into a 200 ml jacketed glass reactor fitted with a gas inlet, with a condenser (−78° C.) mounted over it and conditioned under helium. The reagents are introduced by syringe through a septum. Heating is provided by circulating oil through the reactor jacket. Stirring is carried out by a magnetic bath. After cooling, a sample of liquid is withdrawn by syringe and assayed by a chromatographic method in order to determine the degree of conversion of the haloolefin and the selectivity and yield of halohydrocarbon.

EXAMPLES

In the examples below, the degree of conversion is the ratio between the initial haloolefin concentration minus its final concentration, divided by the initial concentration, multiplied by 100; the halohydrocarbon selectivity is the ratio between the final halohydrocarbon concentration divided by the initial haloolefin concentration minus its final concentration, multiplied by 100; the yield of halohydrocarbon is the ratio between the final halohydrocarbon concentration divided by the initial haloolefin concentration, multiplied by 100.

Example 1 (in accordance with the invention)

In this example, 1,1,1,3,3-pentachlorobutane was prepared by reaction between 2-chloro-1-propene, carbon tetrachloride in the presence of nickel catalyst of formula I in which R represents hydrogen and X represents a bromide ion, and in the presence of propionitrile in the molar ratios 1/4/0.01/9. The reaction is carried out at a temperature of 40° C. for 3 hours. The 1,1,1,3,3-pentachlorobutane is obtained in a yield of 67%, a selectivity of 86% and a degree of conversion of the haloolefin of 78%.

Example 2 (in accordance with the invention)

In this example, 1,1,1,3,3-pentachlorobutane was prepared by reaction between 2-chloro-1-propene, carbon tetrachloride in the presence of nickel catalyst of formula I in which R represents hydrogen and X represents a bromide ion, and in the presence of adiponitrile in the molar ratios 1/4/0.02/6. The reaction is carried out at a temperature of 40° C. for 1 hour. The 1,1,1,3,3-pentachlorobutane is obtained in a yield of 79%, a selectivity of 88% and a degree of conversion of the haloolefin of 90%.

What is claimed is:

1. A process for the preparation of halohydrocarbons comprising at least 3 carbon atoms, wherein a haloalkane selected from the group consisting of saturated organic compounds containing at least two chlorine atoms and a haloolefine selected from the group consisting of haloethene and halopropene derivatives are reacted in the presence of an organonickel compound catalyst.

2. The process of claim 1, wherein the organonickel compound is chosen from nickel (II) salts formed with carboxylic acids, and from organometallic compounds in which the nickel is attached to an aliphatic or aromatic carbon atom.

3. The process of claim 2, wherein the organonickel compound is chosen from organometallic compounds in which the nickel is attached to an aromatic carbon atom.

4. The process of claim 3, wherein the organonickel compound corresponds to the general formula $[Ni^{III}\{4\text{-}RC_6H_2(CH_2NMe_2)_2\text{-}2,6\}X]0$ in which R represents a hydrogen atom or an electron-donating group and X represents a halide ion.

5. The process of claim 1, wherein the reaction takes place in the presence of a solvent.

6. The process of claim 5, wherein the solvent is an aliphatic or aromatic nitrile.

7. The process of claim 1, wherein the molar ratio between the organonickel compound and the haloolefin is greater than or equal to 0.0001 and less than or equal to 1, and the molar ratio between the haloalkane and the haloolefin is greater than or equal to 0.1 and less than or equal to 20.

8. The process of claim 1, wherein the haloalkane is chosen from saturated organic compounds containing from one to three carbon atoms and at least 2 chlorine atoms, and the haloolefin is a haloethene or halopropene derivative.

9. The process of claim 8, wherein the halohydrocarbon is 1,1,1,3,3-pentachlorobutane or 1,1,1,3,3-pentachloropropane.

10. The process of claim 1, wherein the reaction takes place at a temperature greater than 30° C. and less than 70° C.

11. The process of claim 1, wherein the haloalkane is carbon tetrachloride, and the haloolefin is vinyl chloride, vinylidene chloride, trichloroethylene, 1-chloro-1-propene, 2-chloro-1-propene or 3-chloro-1-propene.

* * * * *